United States Patent [19]

Code

[11] Patent Number: 4,986,817
[45] Date of Patent: Jan. 22, 1991

[54] HYPODERMIC SYRINGE SHEATH HOLDER AND NEEDLE GUIDE

[75] Inventor: James Code, Texarkana, Tex.

[73] Assignee: International Development Systems, Inc., Fort Smith, Ark.

[21] Appl. No.: 275,333

[22] Filed: Nov. 22, 1988

[51] Int. Cl.$^5$ .............................................. A61M 5/32
[52] U.S. Cl. ....................................... 604/192; 604/263
[58] Field of Search ........................ 604/192, 263, 187

[56] References Cited

U.S. PATENT DOCUMENTS

| | | | |
|---|---|---|---|
| 4,485,918 | 12/1984 | Mayer | 604/263 X |
| 4,559,042 | 12/1985 | Votel | 604/192 |
| 4,610,667 | 9/1986 | Pedicano et al. | 604/263 |
| 4,623,336 | 11/1986 | Pedicano et al. | 604/192 |
| 4,629,453 | 12/1986 | Cooper | 604/192 |
| 4,636,201 | 1/1987 | Ambrose et al. | 604/192 |
| 4,654,034 | 3/1987 | Masters et al. | 604/192 |
| 4,659,330 | 4/1987 | Nelson et al. | 604/192 |
| 4,717,386 | 1/1988 | Simmons | 604/192 |
| 4,742,910 | 5/1988 | Staebler | 604/192 X |
| 4,767,412 | 8/1988 | Hymanson | 604/192 |

FOREIGN PATENT DOCUMENTS

| | | | |
|---|---|---|---|
| 3433359 | 4/1986 | Fed. Rep. of Germany | 604/192 |
| 2586568 | 3/1987 | France | 604/263 |
| 85/00003 | 1/1985 | PCT Int'l Appl. | 604/192 |

Primary Examiner—John D. Yasko
Attorney, Agent, or Firm—Ross, Howison, Clapp & Korn

[57] ABSTRACT

A safety device for uncapping and recapping a removable protective sheath of a needle includes a cylindrical elongated enclosure. The cylindrical elongated enclosure includes first and second ends and a diameter of sufficient size for receiving and enclosing the sheath. Retaining structure is disposed at the first end of the cylindrical elongated enclosure for grasping and retaining the sheath within the cylindrical elongated enclosure during uncapping and recapping of a needle. Receiving structure communicates with the first end of the cylindrical elongated enclosure for guiding the needle towards the first end of the cylindrical elongated enclosure during recapping and for guiding the sheath toward the first end of the cylindrical elongated enclosure during uncapping.

4 Claims, 3 Drawing Sheets

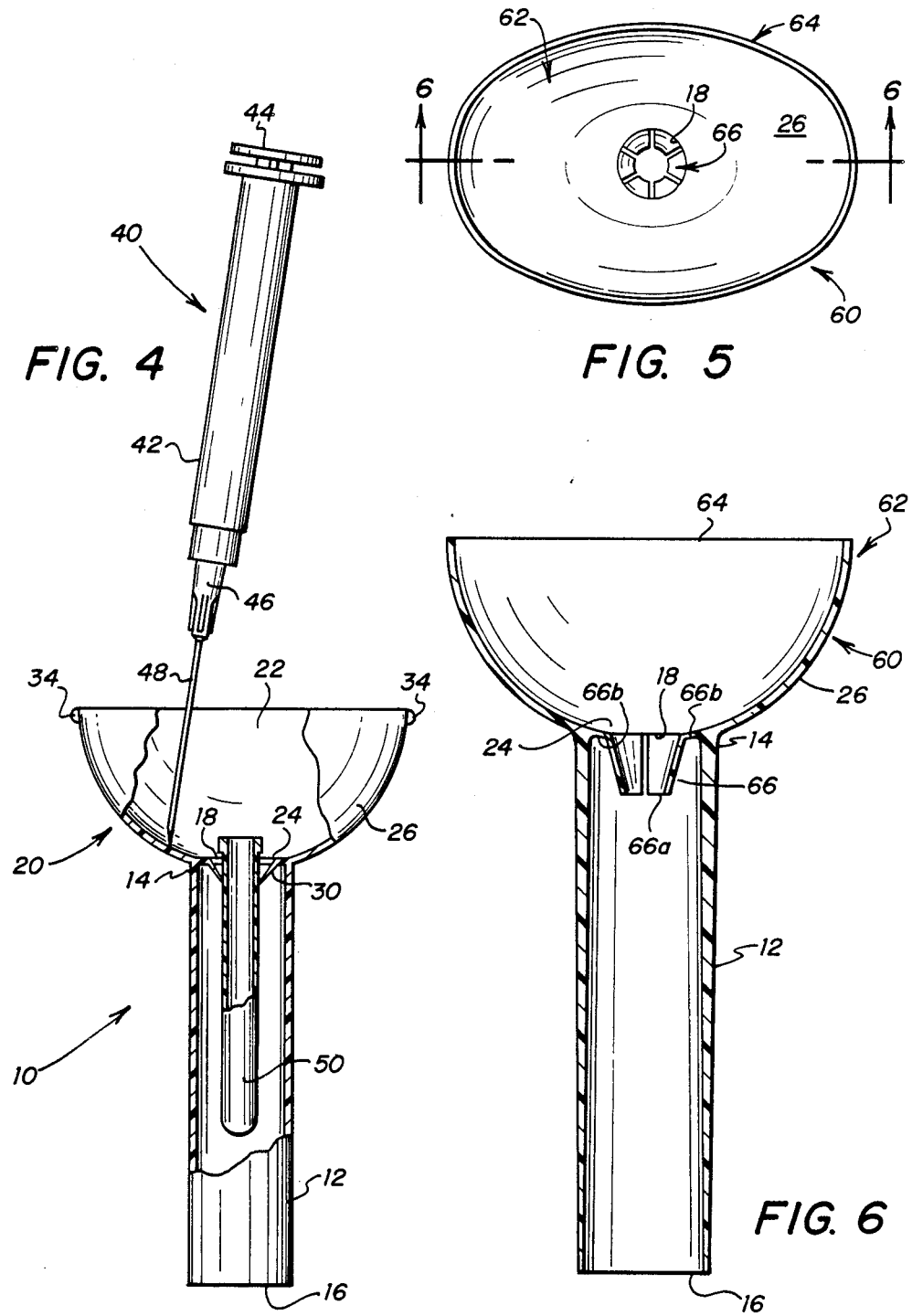

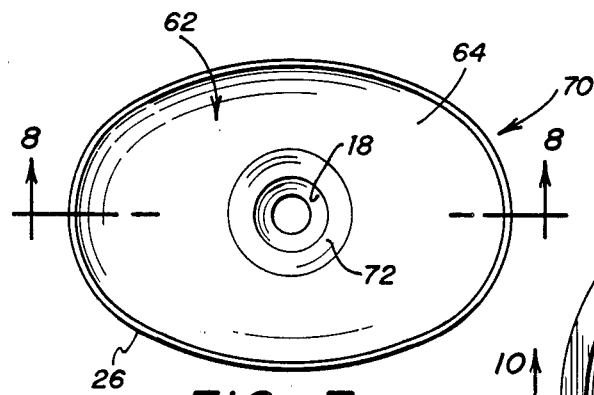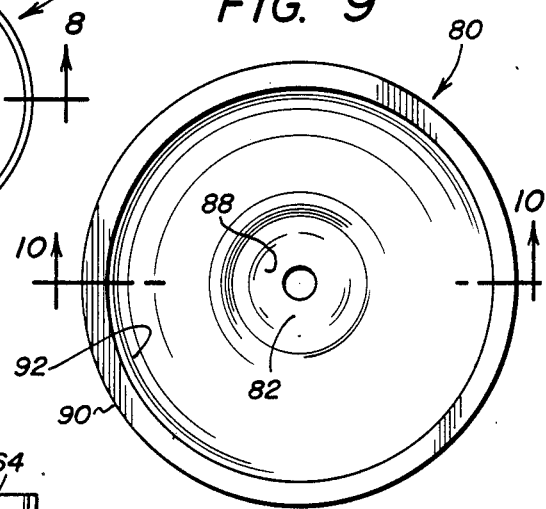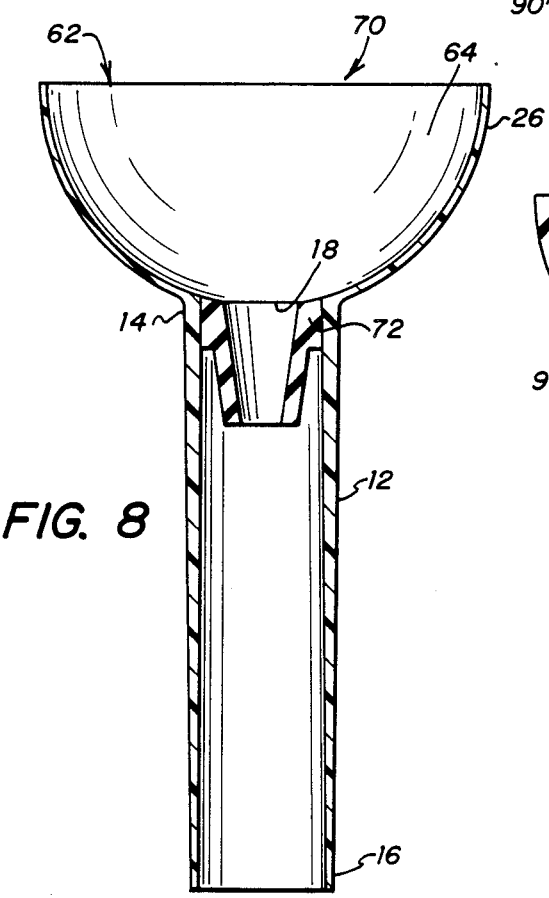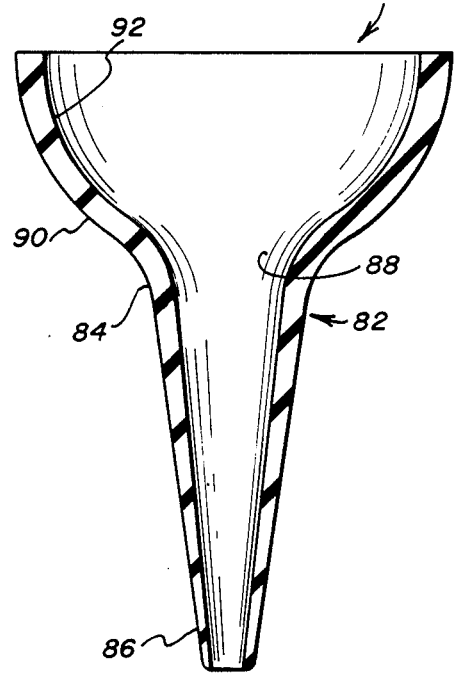

HYPODERMIC SYRINGE SHEATH HOLDER AND NEEDLE GUIDE

TECHNICAL FIELD

This invention relates to safety devices for medical instruments, and more particularly to a safety device for uncapping and recapping the protective sheath of a hypodermic syringe needle.

BACKGROUND OF THE INVENTION

A typical hypodermic syringe has a hollow needle at one end of a cylindrical fluid container and a moveable plunger at the opposite end of the fluid container. The plunger is used to discharge fluid from the fluid container through the needle, or to draw fluid through the needle into the cylindrical fluid container. In order that the needle enter painlessly into the skin, the needle tip usually has a small cross-sectional area and is extremely sharp. Because of the sharpness of the syringe needle, use of the syringe requires great care, since even the most casual contact of the needle with the skin is likely to penetrate the skin, a circumstance commonly known as a "needle stick". The term "needle stick" as used herein, refers to an unintentional or accidental penetration of the skin by a hypodermic syringe needle.

Although a needle stick is a minor injury, it carries the threat of transmitting such diseases as hepatitis and AIDS. Additionally, undesired drugs or toxins may be accidentally transmitted by a needle stick. In order to alleviate the problems of needle stick, a removable protective sheath or cap, is installed over the needle. The protective sheath is an elongated sleeve which is slightly longer than the needle. The sheath is closed at one end and has an opposite end that pressfits onto the base of the needle support structure of the syringe. The sheath is relatively narrow and protects the needle while permitting safe handing of the syringe when the syringe is not in use.

Before using the syringe, the protective sheath must be removed from the needle, a procedure known as uncapping. During uncapping, the sheath is normally gripped between the fingers of one hand, while the other hand holds the cylinder or main body portion of the syringe. Any contact between the needle tip and the hand during the uncapping process can cause a needle stick.

After the syringe has been used, the protective sheath is often replaced over the needle, a procedure known as recapping. During recapping, the protective sheath is again held in one hand and the main body of the syringe is held in the other hand. Any shake of the hand and any misalignment of the needle and sheath during recapping is likely to result in a needle stick to the hand which holds the sheath. Therefore, the problem of needle sticks during recapping is significant.

A need has thus arisen for a safety device for preventing needle stick during uncapping and recapping of a needle of a hypodermic syringe. Such a safety device must be easy to use and fast in operation while providing protection to the user against needle stick.

SUMMARY OF THE INVENTION

A safety device for uncapping and recapping a removable protective sheath of a needle is provided and includes a cylindrical elongated enclosure. The cylindrical elongated enclosure includes first and second ends and a diameter of sufficient size for receiving and enclosing the sheath. Retaining structure is disposed at the first end of the cylindrical elongated enclosure for grasping and retaining the sheath within the cylindrical elongated enclosure during uncapping and recapping of a needle. Receiving structure communicates with the first end of the cylindrical elongated enclosure for guiding the needle towards the first end of the cylindrical elongated enclosure during recapping and for guiding the sheath toward the first end of the cylindrical elongated enclosure during uncapping.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 4 is a side elevational view, partially broken to illustrate insertion of the needle during recapping;

FIG. 5 is a top view of an additional embodiment of the present safety device;

FIG. 6 is a sectional view taken generally along sectional lines 6—6 of FIG. 5;

FIG. 7 is a top view of an additional embodiment of the present safety device;

FIG. 8 is a sectional view taken generally along sectional lines 8—8 of FIG. 7;

FIG. 9 is a top view of an additional embodiment of the present safety device; and FIG. 10 is a sectional view taken along sectional lines 10—10 of FIG. 9.

DESCRIPTION OF THE PREFERRED EMBODIMENTS

Figure 1:
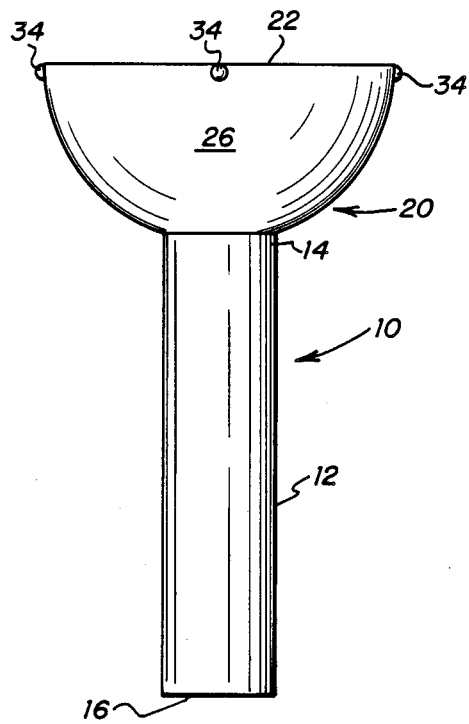
FIG. 1 is a side view of one embodiment of the present safety device.
Figure 2:
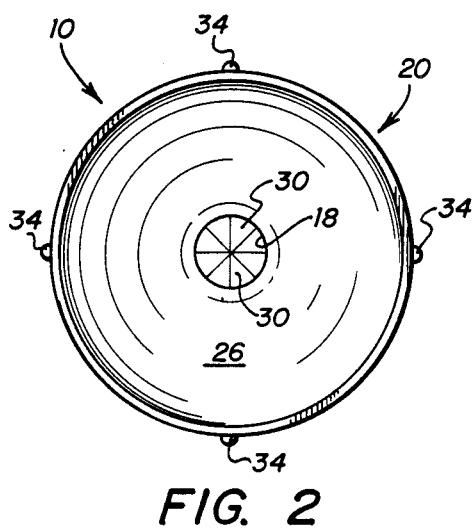
FIG. 2 is a top view of the safety device illustrated in FIG. 1.

Referring simultaneously to FIGS. 1 and 2, the present safety device is illustrated and is generally identified by the numeral 10. Safety device 10 is utilized for uncapping and recapping a removable protective sheath from a conventional hypodermic syringe needle of various sizes and configurations, including but not limited to, syringes used in dental applications. Safety device 10 includes a cylindrical elongated enclosure 12 having a first end 14 and a second end 16. First end 14 includes an aperture 18. Cylindrical elongated enclosure 12 is sized of a sufficient diameter and length for receiving and enclosing the sheath of the hypodermic syringe needle.

Attached to first end 14 of cylindrical elongated enclosure 12 is a funnel-like structure 20 having a large-diameter opening 22 and a small-diameter opening 24. Small-diameter opening 24 of funnel-like structure 20 is disposed adjacent to first end 14 and communicates with cylindrical elongated enclosure 12 through aperture 18. Opening 22 and 24 of funnel-like structure 20 are interconnected via curvilinear sidewalls 26. Opening 22 has a generally circular shape.

Disposed at first end 14 of cylindrical elongated enclosure 12 and across aperture 18 is a plurality of retaining flanges 30 (FIG. 2) which selectively close first end 14 of cylindrical elongated enclosure 12 in the absence of a protective sheath of the hypodermic syringe needle. Retaining flanges 30 frictionally grasp and retain the sheath within cylindrical elongated enclosure 12 during recapping and uncapping of a hypodermic syringe needle.

Disposed along curvilinear sidewalls 26 of funnel-like structure 20, are a plurality of beads 34 which prevent rotation of safety device 10 when disposed on a flat surface.

Figure 3:
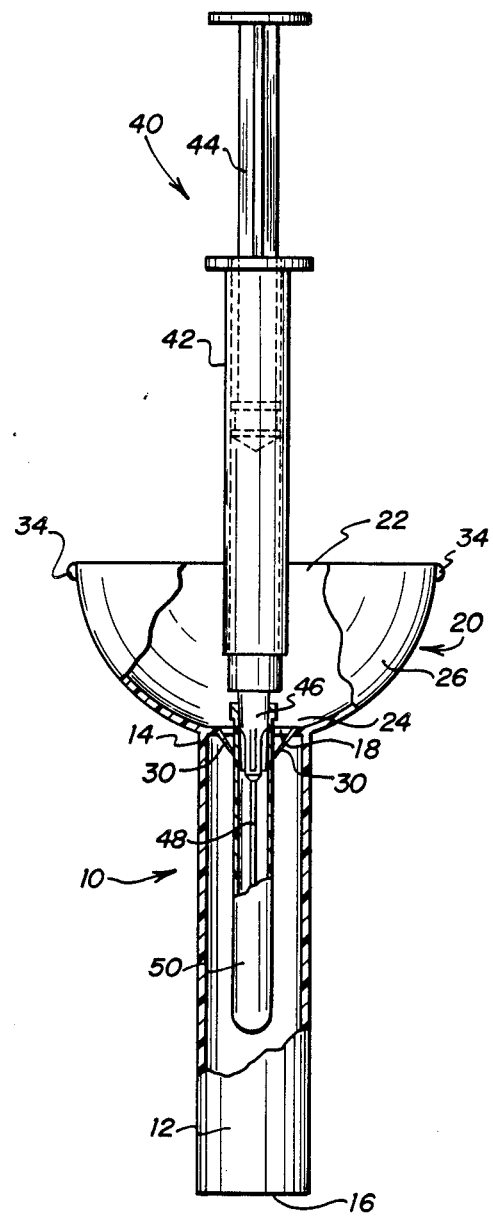
FIG. 3 is a side elevational view, partially broken to illustrate insertion of the syringe and sheath during uncapping.

Referring now to FIG. 3, safety device 10 is illustrated with a hypodermic syringe, generally identified by the numeral 40 inserted therein for uncapping. Hypodermic syringe 40 generally includes a barrel 42 for holding fluid, a plunger 44 used to draw fluid into barrel 42 or to eject fluid, a needle holder 46 at one end of barrel 42 which is usually an integral part of the barrel 42, and a hollow needle 48 through which the fluid passes into or out of the body of a patient. Hollow needle 48 is covered by sheath 50 to protect the user of hypodermic syringe 40 from needle stick.

In order to remove sheath 50 from hypodermic syringe 40 utilizing the present safety device 10, the user places his fingers of one hand around cylindrical elongated enclosure 12 below funnel-like structure 20, and with the other hand inserts hypodermic syringe 40 into safety device 10, such that sheath 50 is inserted through aperture 18 and first end 14 of cylindrical elongated enclosure 12 as illustrated in FIG. 3. Retaining flanges 30 initially, partially closing aperture 18 of first end 14 of cylindrical elongated enclosure 12 are now depressed into cylindrical elongated enclosure 12 to thereby frictionally engage and retain sheath 50 so that hypodermic syringe 40 can be easily removed from sheath 50 during the uncapping procedure. Safety device 10 therefore conveniently retains sheath 50 for recapping of hypodermic syringe needle 48 and prevents loss of sheath 50 during use of hypodermic syringe 40. Curvilinear sidewalls 26 of funnel-like structure 20 assist in guiding sheath 50 to aperture 18 during the uncapping procedure.

Referring now to FIG. 4, hypodermic syringe 40 is illustrated for insertion back into sheath 50 during a recapping procedure. The user of safety device 10 positions his hands similarly to the positions during the uncapping procedure. Curvilinear sidewalls 26 of funnel-like structure 20 assist in guiding needle 48 to aperture 18. Once hypodermic syringe 40 has been inserted into sheath 50, the assembled combination of hypodermic syringe 40 and sheath 50 can be rotated such that sheath 50 frictionally engages needle holder 46, and hypodermic syringe 40 can then be withdrawn from cylindrical elongated enclosure 12 with sheath 50 attached thereto. Retaining flanges 30 then return to the position as illustrated in FIGS. 1 and 2.

Referring simultaneously to FIGS. 5 and 6, a further embodiment of the present safety device is illustrated, and is generally identified by the numeral 60. Like reference numerals are utilized for like and corresponding components previously identified with respect to safety device 10. Attached to first end 14 of cylindrical elongated enclosure 12 is a funnel-like structure 62 having a large-diameter opening 64 of a generally elliptical shape.

Disposed within aperture 18 are a plurality of retaining flanges 66, which extend partially into aperture 18 for frictionally grasping and retaining the sheath within cylindrical elongated enclosure 12 during recapping and uncapping of a hypodermic syringe needle. Flanges 66 include a portion 66a extending between the sidewalls of cylindrical elongated enclosure 12 which spread outwardly when a protective sheath is inserted into cylindrical elongated enclosure 12. A portion 66b of curvilinear sidewalls 26, interconnecting retaining flange 66 to funnel-like structure 62, acts as a stress-relief when a protective sheath is received by safety device 60.

Referring now to FIGS. 7 and 8, an additional embodiment of the present safety device is illustrated and is generally identified by the numeral 70. Like numerals are utilized for like and corresponding components previously identified with respect to safety device 60 shwon in FIGS. 5 and 6. Safety device 70 includes a resilient ring 72 disposed within aperture 18 and extending into cylindrical elongated enclosure 12. Resilient ring 72 frictionally grasps and retains the sheath within cylindrical elongated enclosure 12 during recapping and uncapping of a hypodermic surgical needle. Resilient ring 72 may comprise, for example, rubber.

Referring now to FIGS. 9 and 10, a further embodiment of the present safety device is illustrated, and is generally identified by the numeral 80. Safety device 80 includes a cone-like enclosure 82 having a first end 84 and a second end 86. First end 84 includes an aperture 88 through which the sheath of a hypodermic syringe needle is inserted. The sheath is frictionally grasped and retained within cone-like enclosure 82 through contact with the sidewalls of cone-like enclosure 82.

Attached to end 84 or cone-like enclosure 82 is a funnel-like structure 90 having a large diameter opening 92. The funnel-like structure 90 operates in a manner similar to funnel-like structure 20 of safety device 10.

Safety devices 10, 60 and 70 may be molded from, for example, ABS or polyethylene plastic materials. Safety device 80 may be molded from flexible rubber-like material such that the user of safety device 80 can conveniently flex cone-like enclosure 82 for grasping a sheath of a hypodermic syringe needle.

Although retaining flanges 30 have been shown with respect to safety device 10, retaining flanges 30 can also be utilized with safety device 60, and, alternatively, flanges 66 illustrated for use with safety device 60 can be utilized with safety device 10.

It therefore can be seen that the present safety device provides for a safe and quick procedure for uncapping and recapping a sheath of a hypodermic syringe needle. The present invention protects the hand of a user during uncapping and recapping by maintaining the hand of the user away from the needle and sheath. The sheath is not handled by the user during uncapping and recapping of the hypodermic needle. However, the sheath can be easily located for recapping since it is retained by the present safety device.

Whereas the present invention has been described with respect to specific embodiments thereof, it will be understood that various changes and modifications will be suggested to one skilled in the art and it is intended to encompass such changes and modifications as fall within the scope of the appended claims.

I claim:
1. A one piece safety device for uncapping and receiving a removable protective sheath of a needle comprising:
   an elongated cone-like structure having first and second ends, said first end having a diameter greater than the diameter of said second end and further including sidewalls interconnecting said ends;

said sidewalls being selectively yieldable for grasping and retaining the sheath within said elongated cone-like structure during uncapping and recapping of the needle;

a funnel-shaped member having a small-diameter opening and a large-diameter opening interconnected by arcuate sidewalls, said small-diameter opening thereof communicating with said first end of said elongated cone-like structure and said large diameter opening thereof receiving the sheath during uncapping and receiving the needle during recapping and said arcuate sidewalls guiding the needle and sheath toward said first end of said elongated cone-like structure; and said elongated cone-like structure and said funnel-shaped member are integrally molded from a resilient member.

2. A one piece safety device for uncapping and receiving a removable protective sheath of a needle comprising:

an elongated cone-like structure having first and second ends, said first end having a diameter greater than the diameter of said second end and further including sidewalls interconnecting said ends;

said sidewalls being selectively yieldable for grasping and retaining the sheath within said elongated cone-like structure during uncapping and recapping of the needle;

a funnel-shaped member having a small-diameter opening and a large-diameter opening interconnected by arcuate sidewalls, said large-diameter opening of said funnel-shaped member being circularly shaped, said small-diameter opening thereof communicating with said first end of said elongated cone-like structure and said large diameter opening thereof receiving the sheath during uncapping and receiving the needle during recapping and said arcuate sidewalls guiding the needle and sheath toward said first end of said elongated cone-like structure; and said elongated cone-like structure and said funnel-shaped member are integrally molded from a resilient member.

3. A one piece safety device for uncapping and receiving a removable protective sheath of a needle comprising:

an elongated cone-like structure having first and second ends, said first end having a diameter greater than the diameter of said second end and further including sidewalls interconnecting said ends;

said sidewalls being selectively yieldable for grasping and retaining the sheath within said elongated cone-like structure during uncapping and recapping of the needle;

a funnel-shaped member having a small-diameter opening and a large-diameter opening interconnected by arcuate sidewalls, said large-diameter opening of said funnel-shaped member being elliptically shaped, said small-diameter opening thereof communicating with said first end of said elongated cone-like structure and said large diameter opening thereof receiving the sheath during uncapping and receiving the needle during recapping and said arcuate sidewalls guiding the needle and sheath toward said first end of said elongated cone-like structure; and said elongated cone-like structure and said funnel-shaped member are integrally molded from a resilient member.

4. A one piece safety device for uncapping and receiving a removable protective sheath of a needle comprising:

an elongated cone-like structure having first and second ends, said first end having a diameter greater than the diameter of said second end and further including sidewalls interconnecting said ends;

said sidewalls being selectively yieldable for grasping and retaining the sheath within said elongated cone-like structure during uncapping and recapping of the needle;

a funnel-shaped member having a small-diameter opening and a large-diameter opening interconnected by arcuate sidewalls, said small-diameter opening thereof communicating with said first end of said elongated cone-like structure and said large diameter opening thereof receiving the sheath during uncapping and receiving the needle during recapping and said arcuate sidewalls guiding the needle and sheath toward said first end of said elongated cone-like structure;

said elongated cone-like structure and said funnel-shaped member are integrally molded from a resilient member; and means disposed on said funnel-shaped member adjacent said large-diameter opening for preventing rotation of the safety device when the safety device is positioned on a flat surface.

* * * * *